United States Patent
Reed et al.

(10) Patent No.: US 12,370,059 B2
(45) Date of Patent: Jul. 29, 2025

(54) INTERBODY FUSION DEVICES WITH SELF-AFFIXING MECHANISMS

(71) Applicant: GLOBUS MEDICAL, INC., Audubon, PA (US)

(72) Inventors: Don Reed, Philadelphia, PA (US); Aditya Ingalhalikar, Pune (IN); Jeff Nichols, Medford, NJ (US); Brandon Preske, Newtown Square, PA (US); Mark Fromhold, Phoenixville, PA (US); Colm McLaughlin, Glenside, PA (US); Mark Adams, Downingtown, PA (US); Brian Garvey, Media, PA (US)

(73) Assignee: Globus Medical, Inc., Audubon, PA (US)

( * ) Notice: Subject to any disclaimer, the term of this patent is extended or adjusted under 35 U.S.C. 154(b) by 120 days.

(21) Appl. No.: 18/187,832

(22) Filed: Mar. 22, 2023

(65) Prior Publication Data
US 2023/0225878 A1 Jul. 20, 2023

Related U.S. Application Data

(63) Continuation of application No. 17/361,515, filed on Jun. 29, 2021, now Pat. No. 11,642,228, which is a continuation of application No. 15/841,629, filed on Dec. 14, 2017, now Pat. No. 11,076,967, which is a continuation of application No. 15/141,122, filed on
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4611* (2013.01); *A61F 2002/30505* (2013.01); *A61F 2002/30507* (2013.01); *A61F 2002/30525* (2013.01); *A61F 2002/30579* (2013.01); *A61F 2002/30593* (2013.01);
(Continued)

(58) Field of Classification Search
CPC .. A61F 2/30749; A61F 2/4465; A61F 2/4611; A61F 2002/30505; A61F 2002/30507; A61F 2002/30525; A61F 2002/30579; A61F 2002/30787; A61F 2220/0016
See application file for complete search history.

(56) References Cited

U.S. PATENT DOCUMENTS

2008/0312699 A1* 12/2008 Johnson ............. A61B 17/7059
606/280
2009/0164020 A1 6/2009 Janowski et al.
(Continued)

FOREIGN PATENT DOCUMENTS

JP 2012508044 A 4/2012
JP 2012523930 A 10/2012
(Continued)

*Primary Examiner* — Nicholas J Plionis

(57) ABSTRACT

Interbody fusion devices including deployable fixation members. The implant may include a spacer, optionally, an end member coupled to the spacer, and one or more fixation members configured to extend into adjacent vertebrae. The fixation members may include screws, nails, shims, tangs, spikes, staples, pins, blades, fins, or the like, and combinations thereof.

20 Claims, 14 Drawing Sheets

Related U.S. Application Data

Apr. 28, 2016, now Pat. No. 9,872,780, which is a continuation of application No. 14/458,687, filed on Aug. 13, 2014, now Pat. No. 9,351,847.

(60) Provisional application No. 61/868,803, filed on Aug. 22, 2013.

(52) U.S. Cl.
CPC . *A61F 2/30749* (2013.01); *A61F 2002/30787* (2013.01); *A61F 2220/0016* (2013.01)

(56) References Cited

U.S. PATENT DOCUMENTS

| | | |
|---|---|---|
| 2009/0210062 A1 | 8/2009 | Thalgott et al. |
| 2010/0057206 A1 | 3/2010 | Duffield et al. |
| 2010/0305704 A1* | 12/2010 | Messerli ................. A61F 2/442 |
| | | 623/17.16 |
| 2011/0035007 A1 | 2/2011 | Patel et al. |
| 2011/0230971 A1 | 9/2011 | Donner et al. |
| 2012/0078371 A1* | 3/2012 | Gamache ........... A61B 17/0682 |
| | | 623/17.16 |
| 2013/0110242 A1 | 5/2013 | Kirwan et al. |
| 2014/0180417 A1* | 6/2014 | Bergey .................... A61F 2/447 |
| | | 623/17.16 |
| 2016/0151171 A1* | 6/2016 | Mozeleski ......... A61B 17/7059 |
| | | 623/17.16 |

FOREIGN PATENT DOCUMENTS

| | | |
|---|---|---|
| JP | 2013516206 A | 5/2013 |
| WO | 2010121028 A3 | 10/2010 |
| WO | 2011080535 A1 | 7/2011 |
| WO | 2012094647 A2 | 7/2012 |

\* cited by examiner

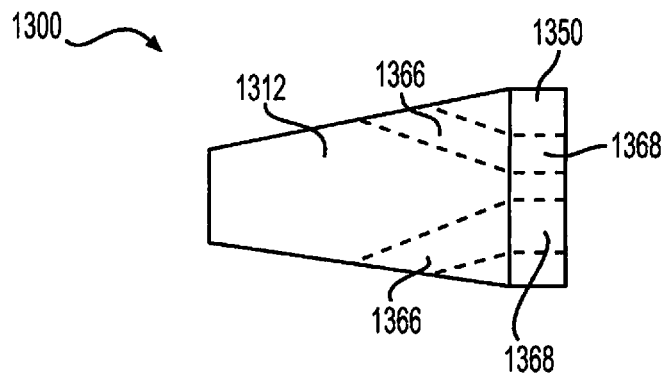
FIG. 19
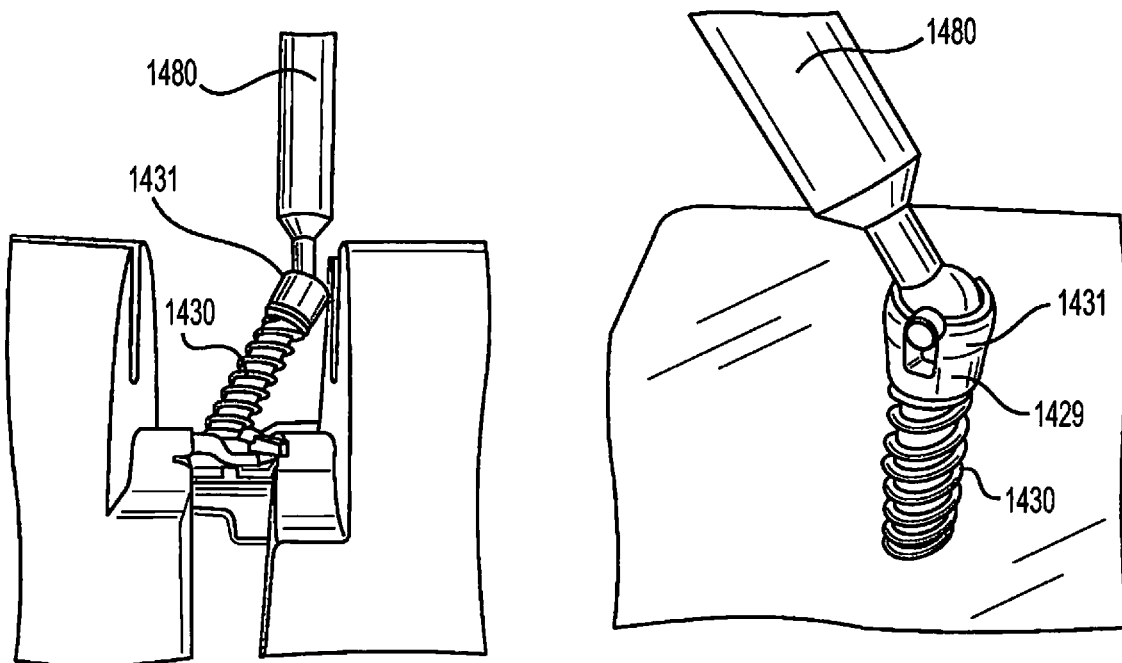
FIG. 20A  FIG. 20B

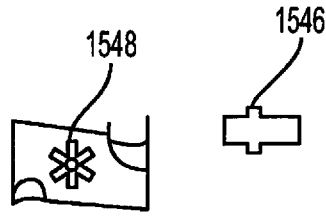
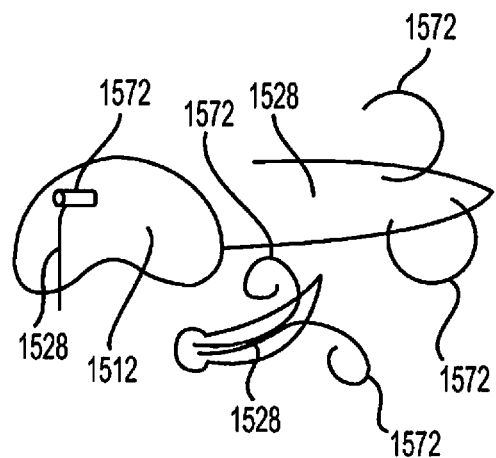
FIG. 21  FIG. 22
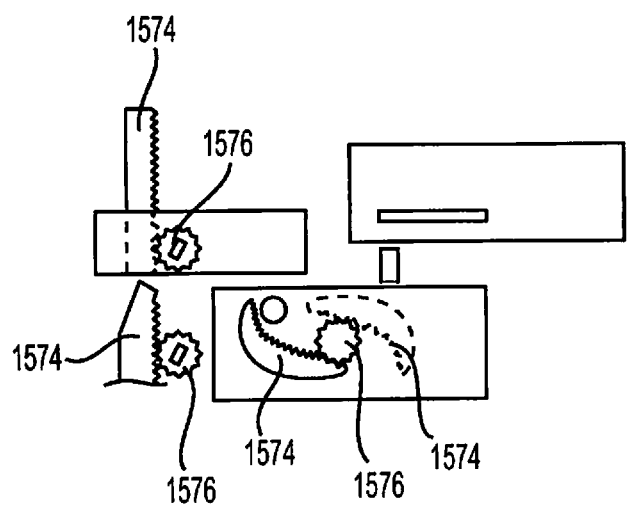
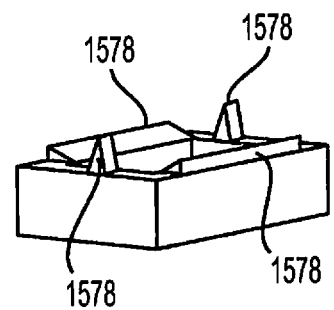
FIG. 23  FIG. 24

INTERBODY FUSION DEVICES WITH SELF-AFFIXING MECHANISMS

CROSS-REFERENCE TO RELATED APPLICATION

The present application is a continuation application of U.S. Ser. No. 17/361,515 filed on Jun. 29, 2021 (published as U.S. Pat. Pub. No. 2021-0322185), which is a continuation application of U.S. Ser. No. 15/841,629 filed on Dec. 14, 2017, now U.S. Pat. No. 11,076,967, which is a continuation application of U.S. Ser. No. 15/141,122, filed Apr. 28, 2016, now U.S. Pat. No. 9,872,780, which is a continuation application of U.S. Ser. No. 14/458,687, filed Aug. 13, 2014, now U.S. Pat. No. 9,351,847, which claims priority to Provisional Application No. 61/868,803 filed Aug. 22, 2013, the entire disclosures of which are incorporated herein by reference in their entireties for all purposes.

FIELD OF THE INVENTION

The present disclosure generally relates to fixation devices for positioning and immobilizing adjacent vertebral bodies. In particular, the devices may include interbody fusion devices.

BACKGROUND OF THE INVENTION

As people age, the intervertebral discs in the spinal column may start to deteriorate. Subsequently, the intervertebral discs being to lose height. As a result of the loss of height between vertebral bodies, the nerves exiting from the spinal canal become compressed and pinched, which causes pain among other neurological deficits. One solution is to insert a spacer in place of the disc to restore the height and to promote fusion between adjacent vertebral bodies to permanently maintain the height restoration. Additional fixation may also be needed to stabilize the spinal segment. A plate is usually provided, and the plate may be positioned on the anterior portions of the adjacent vertebral bodies. In some cases, the profile of the plate becomes obstructive to the anatomy. The approach to the spine is also significant in that a direct anterior approach requires navigation or dissection of vascular anatomy.

As a result, there is a need to provide a spacer having fixation elements to attach the spacer directly to adjacent vertebrae, to limit any profile protruding out of the spine column anteriorly, and to avoid proximal anatomy from a direct anterior approach.

SUMMARY OF THE INVENTION

This application relates to interbody fusion devices with self-affixing mechanisms. Each of the interbody fusion devices can be used following a discectomy to assist in maintaining height between vertebral bodies. While the devices are particularly useful in the anterior spinal column, the devices can be used in different regions of the spine as well.

According to one embodiment, an implant for implantation in a treated area of an intervertebral space between vertebral bodies of a spine includes a spacer, an end member, and at least one fixation member. The spacer has a superior surface and an inferior surface. The spacer may define an opening extending from the superior surface to the inferior surface configured to receive bone graft material. The superior surface and the inferior surface each have a contact area configured to engage adjacent vertebrae. The end member is coupled to the spacer. The end member has at least one hole traversing the end member at an angle. The fixation member is configured to extend through the at least one hole traversing the end member. The fixation member may include a curved shim configured to be hammered into adjacent vertebrae. Shims alone may be used to secure the implant or other fixation members may be used in combination with the shim.

The shim may include a spline extending along at least a portion of a longitudinal axis of the shim. The spline may have the greatest height at a head portion of the shim, which tapers to a smallest height proximate to a distal most end of the shim. The shim may have a flat head portion. Alternatively, the shim may have a rounded head portion including an opening configured to retain an insertion instrument. In another embodiment, the shim may be smooth with a substantially conical shape.

The fixation member may be retained within the end member with a blocking mechanism. The blocking mechanism may include a screw having a head which covers over and/or rests against a portion of the fixation member, thereby preventing unintentional backout. Alternatively, the blocking mechanism may include a spring tab configured to block the fixation member once the fixation member is fully inserted into the end member.

The fixation member may be in a deployable form having a tip configured to expand after implantation. The deployable fixation member may include an inner portion and an outer sleeve. Once the deployable fixation member is inserted into bone, the inner portion is capable of being pulled opposite to the insertion direction to deform and splay the tip of the fixation member open.

According to another embodiment, an implant may include a spacer having a superior surface and an inferior surface. The superior surface and the inferior surface each have a contact area configured to engage adjacent vertebrae. The spacer defines at least one opening extending from the superior surface to the inferior surface. At least one shaft may be coupled to the spacer and extends through the opening in the spacer. One or more fins may be operatively attached to the shaft such that rotation of the shaft causes deployment of the one or more fins configured to engage adjacent vertebral bone when deployed.

The fins may be rotated about 90° between retracted and deployed positions. In one embodiment, the fins may rest on a wall dividing the opening when in the retracted position. In an alternative embodiment, the fins may be sized and shaped such that they are housed within the opening when in the retracted position. The fins may include a plurality of fins attached to a single shaft. Alternatively, more than one shaft may be used with one or more fins positioned on each shaft. The fins may have a sharpened edge configured to cut through the adjacent vertebral bone. The fins may have straight or hooked shapes, for example.

According to another embodiment, an implant may include a spacer having a superior surface and an inferior surface. The spacer may include a ramped surface positioned on a portion of the superior and/or inferior surface. An end member configured to be coupled to the spacer may house or contain one or more blades. As the end member is attached to the spacer, the one or more blades may engage the ramped surface of the spacer, thereby causing the one or more blades to expand outwardly and engage adjacent vertebrae.

The blades may include two blades attached together via a hinge (e.g., a living hinge). The blades may have a first, collapsed orientation before the end member is attached to the spacer, and a second, expanded orientation where the blades are expanded apart such that an angle between the blades is larger than in the collapsed orientation. The ramped surface may be angled such that the ramped surface extends from a central portion of the spacer and increases in height outward toward the lateral portion of the spacer.

BRIEF DESCRIPTION OF THE DRAWINGS

The invention may be best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 19 illustrates an interbody fusion device having a mechanism for facilitating inline operation;

FIGS. 20A and 20B illustrates a universal joint (e.g., a ball joint) that can be built in the head of a bone screw to provide polyaxial adjustability;

FIG. 21 illustrates how deployable nails, fins etc. can be actuated by a worm and/or worm wheel with teeth;

FIG. 22 illustrates an embodiment of an interbody fusion device having deployable barb wires through a curved spike hammered in through the spacer body;

FIG. 23 illustrates an alternative interbody fusion device including a straight or curved rack and pinion mechanism; and FIG. 24 illustrates a keeled connection between a spacer and a vertebral body.

DETAILED DESCRIPTION OF THE INVENTION

Figure 1:
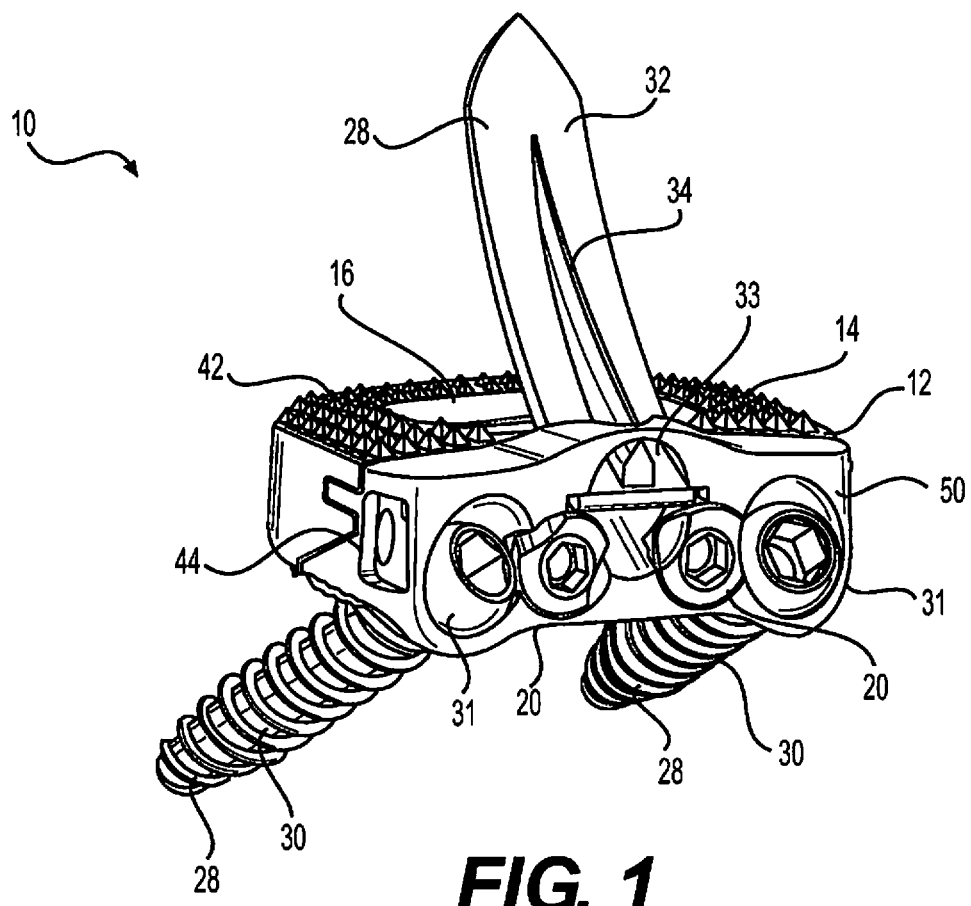
FIG. 1 shows an example of an interbody fusion device implantable in a disc space in accordance with an embodiment of the present application.

Embodiments of the disclosure are generally directed to stand-alone interbody fusion implants. Specifically, the implants include a spacer body. The spacer may be combined with an end member. One or more fixation members, such as screws, nails, shims, tangs, spikes, staples, pins, fins, blades, or the like, may be used to secure the device to adjacent vertebrae. The fixation members may also include a combination of these to provide for optimal ease of insertion and fixation of the device.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Certain embodiments may be used on the cervical, thoracic, lumbar, and/or sacral segments of the spine. The size and mass increase of the vertebrae in the spine from the cervical to the lumbar portions is directly related to an increased capacity for supporting larger loads, for example. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible areas.

Referring now to the figures, FIGS. 1-5 depict alternative embodiments of an interbody fusion device 10 having different types of fixation members 28 designed to secure the fusion device 10 to adjacent vertebral bodies. The fixation members 28 may be in the form of one or more screws 30, nails or shims 32, or the like.

With reference to FIG. 1, an example of an interbody fusion device 10 in accordance with one embodiment of the present application is shown, which is implantable in a disc space. The device may comprise a spacer or body portion 12 affixed to an end member 50. The body portion 12 may be in the form of a spacer or cage having an opening 16 that may serve as a graft opening for receiving graft material. The body portion 12 can include a contact area having one or more protrusions 14, for example, in the form of teeth, ridges, or ribs on either or both of its superior and inferior surfaces 42, 44 to prevent expulsion of the body portion 12 between adjacent vertebrae. The body portion 12 can be formed of PEEK (polyether ether ketone), other plastics, titanium, other metal or metal alloys, or other suitable bio-compatible materials known in the art.

The spacer or body portion 12 and the end member 50 may be coupled, removably coupled, connected, or attached together in any suitable manner known in the art. The body portion 12 and the end member 50 may be coupled together through appropriate coupling means or fasteners. For example, at least a portion of the end member 50 and/or body portion 12 may be configured to provide male and female projections and recesses, which act as the mechanical interfaces between the two pieces. The body portion 12 and the end member 50 may be assembled together using, alone or in combination, a friction fit, a dovetail assembly, dowel pins, hooks, staples, screws, adhesives, and the like, or any suitable fasteners known in the art. The end member 50, which can be formed of metal, for example, can include one or more openings for receiving one or more fixation members 28 therethrough. The openings may be angled such that the openings extend through the end member 50 at an angle divergent to a horizontal plane. The end member 50 may be contoured any may include one or more eyebrows, for example, to accommodate the angled trajectory of the fixation members 28.

The fixation members 28 are configured to extend into a vertebral body to provide vertebral fixation. The fixation members 28 may include one or more components designed to secure the device to adjacent vertebrae. By way of example, the fixation members 28 may be selected from screws, nails, shims, staples, pins, or the like, and combinations thereof. As shown in FIG. 1, the fixation members 28 can include one or more bone screws 30 (facing downward in FIG. 1), as well as one or more thinner nails or shims 32 (facing upward in FIG. 1).

The bone screws 30 may include a threaded shaft and a head portion 31. The head portion 31 may be rounded. The screws 30 may include any suitable screws known in the art including fixed or variable angle of any suitable size with appropriate thread spacing, thread pitch, head design, length, and the like. The screws 30 enter the screw holes in the end member 50 at specified angles to enter each of the adjacent vertebrae at the optimal locations. In particular, the screws 30 may be inserted at an angle for maximum screw purchase into the superior and/or inferior vertebral bodies.

The shims 32 may include a substantially flat or thin piece of material extending along a longitudinal axis. In some embodiments, the one or more shims 32 can be curved or angled, while in other embodiments, the one or more shims 32 can be straight. While bone screws 30 provide strength, in some situations, it may desirable to use a thinner nail or shim 32, as such fixation members 28 can be easily inserted. In some embodiments, the bone screw 30 is screwed into bone (e.g., using a driver), while the shim 32 can be hammered into place. The shim 32 may include a head portion 33 which is substantially flattened at its proximal most end. The flattened head portion 33 may allow for greater contact area with an insertion instrument, for example, when the shim 32 is hammered into place. The shims 32 may include a rounded or pointed tip at the distal most end. The shims 32 may or may not contain an extension or spline 34. If present, the spline 34 may be positioned at any suitable location along the shim 32. For example, the spline 34 may extend along at least a portion of the longitudinal axis of the shim 32. The spline 34 may also extend to the head portion 33. The spline 34 may have the greatest height at the head portion 33 and taper to the smallest height proximate to the distal most end of the shim 32. A cross piece may be positioned below the spline 34 and across the head portion 33, for example, to further secure the shim 32 to the end member 50 and/or stabilize the device 10.

While FIG. 1 shows two bone screws 30 and one shim 32, in other embodiments, the device can include different numbers, types, and variations of bone screws 30 and/or shims 32. For example, in some embodiments, the device can be fixed to adjacent vertebrae using only shims 32 (e.g., via three or more shims 32). The fixation members 28 can not only provide a means of fixation between the device 10 and vertebrae, but in some embodiments, can also help lag vertebral bone down to the spacer body 12.

In some embodiments, the fixation members 28 can be pre-assembled with the body portion 12 as the body portion 12 is inserted into the disc space. The fixation members 28 would simply need to be deployed into the vertebral bodies once the cage body is in a desired surgical site. In other embodiments, the fixation members 28 can be inserted into the body portion 12 after the body portion 12 is inserted into a disc space.

In addition to having one or more openings for receiving one or more fixation members 28, the end member 50 can include one or more openings to retain one or more blocking mechanisms 20 to prevent undesirable backout of the fixation members 28 (e.g., screws 30 or shims 32). As shown in FIG. 1, the device 10 can include two or more blocking mechanisms 20 (e.g., blocking screws) that prevent backout. In some embodiments, the blocking mechanism 20 can prevent backout of one or more fixation members 28 (e.g., a bone screw 30 or a nail/shim 32). In other embodiments, the blocking mechanism 20 can prevent backout of two or more fixation members 28 (e.g., a bone screw 30 and a nail/shim 32). For example, as shown in FIG. 1, each blocking mechanism 20 serves to block both the bone screw 30 and the shim 32 from unintended backout. In some embodiments, the blocking mechanism 20 includes a cut-out portion that allows for insertion of the fixation member 28 through the end member 50. Once the fixation member 28 is inserted through the end member 50, the blocking mechanism 20 can be rotated, such that at least a portion of the blocking mechanism 20 covers over and/or rests against a portion of the fixation member 28, thereby preventing unintentional backout.

Figure 2:
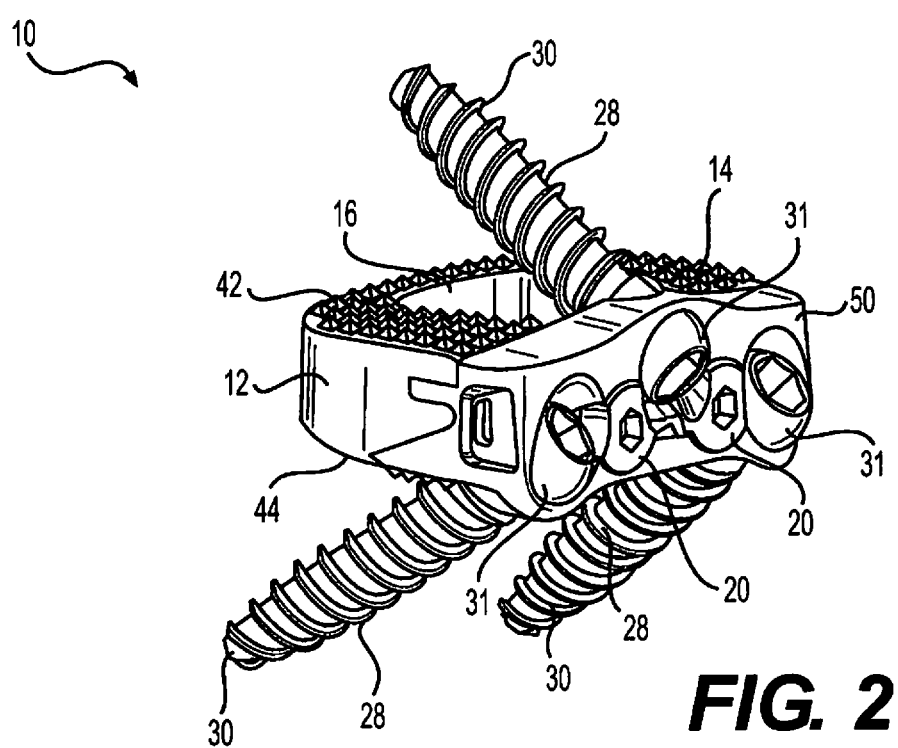
FIG. 2 depicts an alternative embodiment of an interbody fusion device with self-affixing mechanisms.

Referring now to FIG. 2, an alternative embodiment of an interbody fusion device 10 is shown with self-affixing mechanisms. This device 10 includes similar features as the device described in FIG. 1, including body portion 12, end member 50, one or more fixation members 28, and one or more blocking mechanisms 20. However, the present device 10 utilizes three fixation members 28—each comprising a bone screw 30 for maximum fixation. As shown in FIG. 2, two of the bone screws 30 face downwardly, while one of the bone screws 30 faces upwardly.

Figure 3:
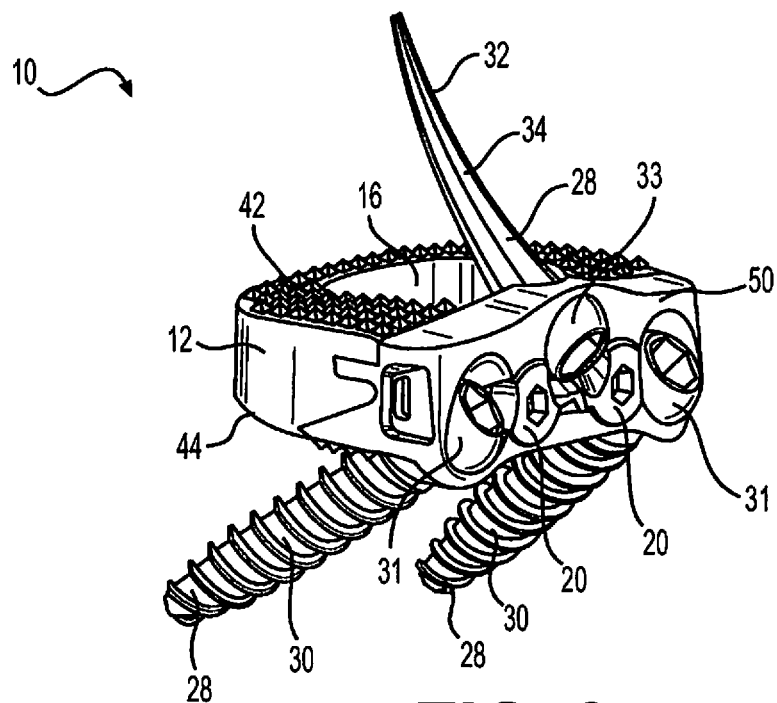
FIG. 3 shows an alternative embodiment of an interbody fusion device with self-affixing mechanisms.

As shown in FIG. 3, an alternative embodiment of an interbody fusion device 10 with self-affixing mechanisms is shown. This device 10 includes similar features as the device described in FIG. 1, including the body portion 12, the end member 50, one or more fixation members 28, and one or more blocking mechanisms 20. As shown in FIG. 3, the fixation members 28 can include one or more bone screws 30 (facing downward in FIG. 3), as well as one or more thinner nails or shims 32 (facing upward in FIG. 3). However, the present device 10 utilizes a distinct upwardly facing nail or shim 32 that is slender and tapered. This shim 32, which is curved in FIG. 3, advantageously accommodates easy insertion into a vertebral body.

Note that in the present embodiment, the shim 32 has a rounded head portion 33, similar to the head portions 31 of the bone screws 30. The rounded head 33 may include an opening, for example, configured to retain an insertion instrument. This is in contrast to the shim 32 in FIG. 1, which does not have a rounded head portion 33, but rather is substantially flattened at its proximal most end. The rounded head 33 of the shim 32 advantageously provides a mechanism for preventing over-insertion of the shim 32 into the device 10. Likewise, however, the substantially flattened shim 32 in FIG. 1 can also provide its own mechanism, such as a tab or particularly shaped feature that prevents over-insertion of the shim 32 in the fusion device 10. Similar to FIG. 1, the shims 32 may include a spline 34. The spline 34 may extend along at least a portion of the longitudinal axis of the shim 32. In this case, the spline 34 extends along the entire length of the shim 32. The shim 32 is also provided with a pointed tip at the distal most end.

Figure 4:
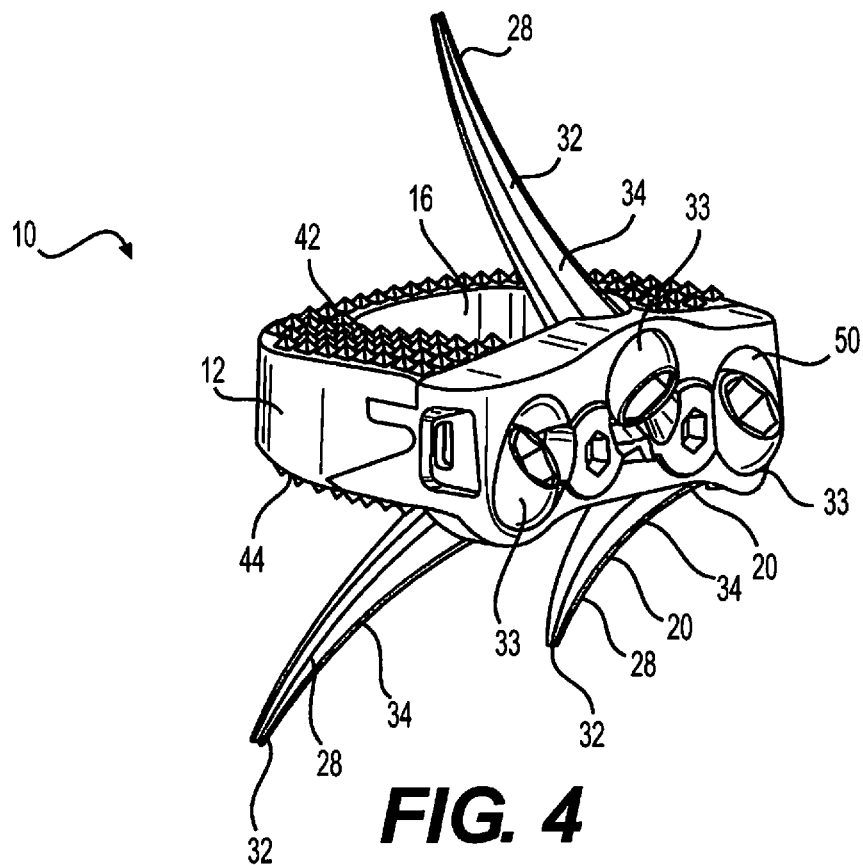
FIG. 4 depicts an alternative embodiment of an interbody fusion device with self-affixing mechanisms.

FIG. 4 shows an alternative embodiment of an interbody fusion device 10 with self-affixing mechanisms in accordance with one embodiment. This device 10 includes similar features as the device described in FIG. 1, including body portion 12, end member 50, one or more fixation members 28, and one or more blocking mechanisms 20. However, in the present device 10, the three fixation devices 28 are each slender, tapered nails or shims 32. Each of the shims 32 is curved and designed to provide easy access into a vertebral body.

Figure 5:
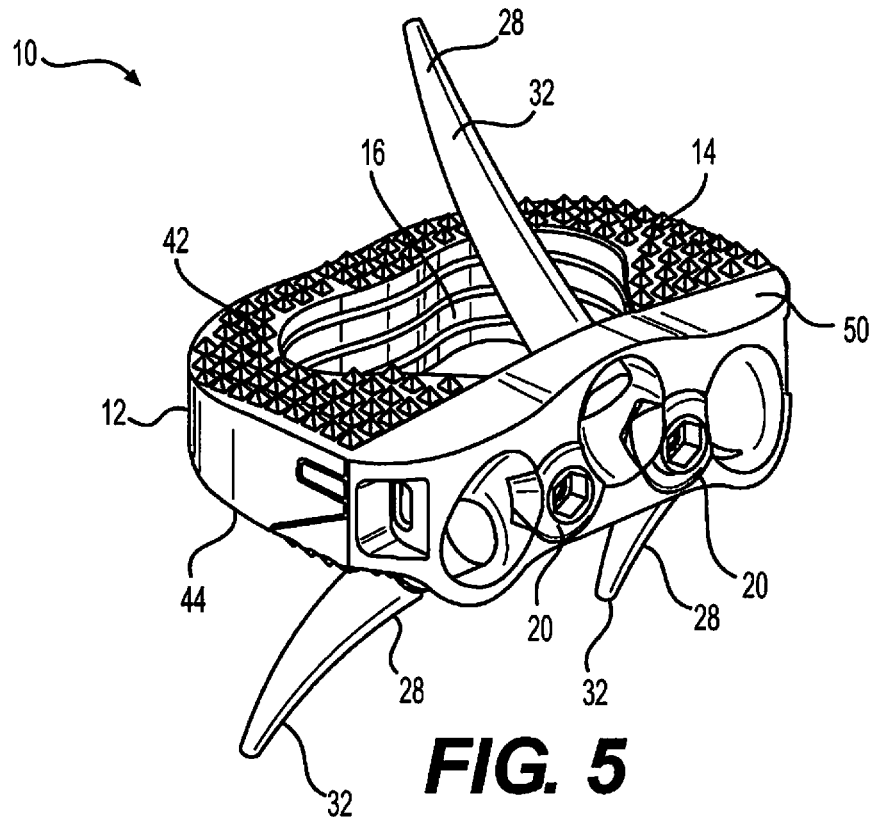
FIG. 5 shows an alternative embodiment of an interbody fusion device with self-affixing mechanisms.

FIG. 5 shows an alternative embodiment of an interbody fusion device 10 with self-affixing mechanisms in accordance with one embodiment. This device 10 includes similar features as the device described in FIG. 1, including body portion 12, end member 50, one or more fixation members 28, and one or more blocking mechanisms 20. However, in the present device 10, the fixation members 28 comprise three smoothened shims or nails 32 that can be inserted into a vertebral body. These nails 32 may be substantially conical in shape and do not include splines. The nails 32 may or may not include a head portion, and as shown, the nails 32 may be substantially flattened at its proximal most end. The nails 32 may include a rounded or pointed tip at the distal most end. In some embodiments, the nails 32 can be straight or, as shown in FIG. 5, may be curved, with a minimum of one in the superior direction and one in the inferior direction. The shims or nails 32 can be pressed through the spacer body 12 and retained partially within the spacer body 12. The nails 32 can be held within the spacer body 32 by a component such as a blocking screw 20. In some embodiments, the shims or nails 32 can be held in position via a spring tab (see FIGS. 10A and B).

Figure 6:
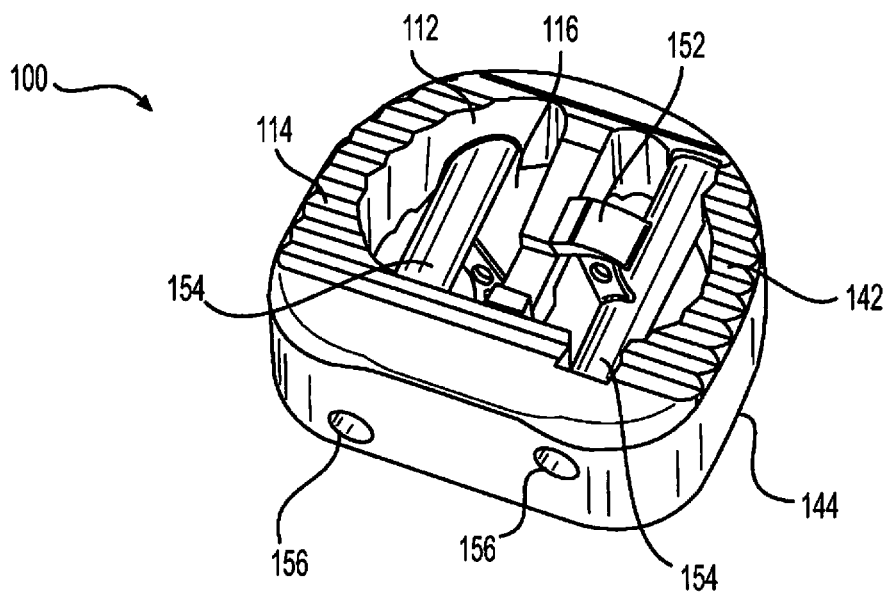
FIG. 6 illustrates a top perspective view of an alternative interbody fusion device including a spacer body with deployable fins on multiple shafts.

FIG. 6 illustrates a top perspective view of an alternative interbody fusion device 100 including a spacer body 112 in accordance with some embodiments of the present application. The spacer body 112 may be in the form of a spacer or cage having one or more openings 116 that may serve as a graft opening for receiving graft material. As shown, the opening 116 may be divided into two equal parts separated by a central wall. The spacer body 112 can include a contact area having one or more protrusions 114, for example, in the form of teeth, ridges, or ribs on either or both of its superior and inferior surfaces 142, 144 to prevent expulsion of the spacer body 112 between adjacent vertebrae. In the present embodiment, the spacer body 112 is configured to have one or more ridges on a least a portion of its superior and inferior surfaces 142, 144. In addition, it is configured to have one or more fins 152 that cut through bone in adjacent vertebrae. The one or more fins 152 can be operatively attached to one or more shafts 154. The shaft 154 may be in the form of a cylinder extending through the opening 116 from a proximal portion to a distal portion of the spacer 112. Rotation of the shaft 154 causes the deployment of the fins 152, which can lodge and engage in adjacent vertebral bone. The fins 152 may have straight or hooked shapes, for example. The fin 152 may have a sharpened edge to facilitate insertion into the adjacent vertebrae.

As shown in FIG. 6, the device 100 can include two or more shafts 154, each with one or more fins 152 attached thereto. The device 100 may be configured such that at least one fin 152 engages a superior vertebra and at least one fin 152 engages an inferior vertebra. As shown, the two shafts 154 may be offset from one another. The spacer body 112 can include one or more actuation openings 156 that provide access to the shafts 154, thereby allowing one or more instruments to rotate and actuate the shafts 154. As shown in FIG. 6, rotation of the shaft 154 in a first direction will cause deployment of the fin 152, for example in a substantially vertical orientation 152 (not shown), whereas rotation of the shaft 154 in a second opposite direction will cause retraction of the fin 152, for example, in a substantially horizontal orientation (in the position shown). In particular, the fin 152 may be rotated about 90° between the retracted and deployed positions. The fins 152 may rest on the wall dividing the opening 116 when in the retracted position. The fins 152 may be sized and shaped such that they are unable to enter the opening 116 when actuated.

Each of the shafts 154 can be operated independently from one another. The interbody fusion device 100 in FIG. 6 can advantageously operate on its own, without the addition of a plate or other fixation members. However, in other embodiments, the device 100 in FIG. 6 can also be fixed to an end member (as described in other embodiments herein), plate, or the like and can include one or more additional fixation members (e.g., bone screws, nails, shims) to provide additional fixation to adjacent vertebral bodies.

Figure 7:
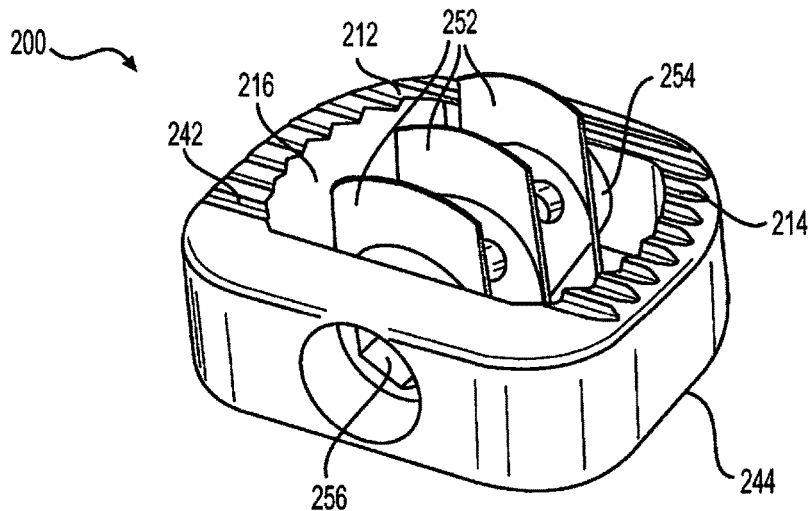
FIG. 7 shows a top perspective view of an alternative interbody fusion device including a spacer body with deployable fins on a single shaft.

FIG. 7 illustrates a top perspective view of an alternative interbody fusion device 200, which is similar to the device 100 shown in FIG. 6. The device 200 includes a spacer body 212. The spacer body 212 may be in the form of a spacer or cage having opening 216 that may serve as a graft opening for receiving graft material. In this embodiment, a single opening 216 is provided in the spacer body 212. Like the fusion device 100 in FIG. 6, the present fusion device 200 includes a plurality of ridges on a least a portion of its superior and inferior surfaces 242, 244, as well as at least one shaft 254 and at least one fin 252. However, in the present embodiment, the fusion device 200 includes only one central shaft 254 with multiple fins 252 extending therefrom (e.g., three upper and three lower fins 252) attached to the shaft 254. The fins 252 may be all of the same height and configuration or may be different. The fins 252 may be coaxially aligned with one another on the shaft 254. The shaft 254 may extend centrally through the opening 216 from a proximal portion to a distal portion of the spacer 212.

The shaft 254 may be provided with one or more openings to allow for egress and/or ingress of graft material. Rotation of the central shaft 254 causes deployment of the multiple fins 252 such that three upper fins 252 can engage an upper vertebra, while three lower fins 252 (not shown) can engage a lower vertebra. To rotate the shaft 254, a driver opening 256 can be provided to accommodate an actuation or driving instrument.

Rotation of the shaft 254 in a first direction will cause deployment of the fins 252, for example, in a substantially vertical orientation (shown in FIG. 7), whereas rotation of the shaft 254 in a second opposite direction will cause retraction of the fins 252, for example, in a substantially horizontal orientation (not shown). In particular, the fins 252 may be rotated about 90° between the retracted and deployed positions. The fins 252 may be sized and shaped such that they are housed within the opening 216 when in the retracted position.

Figure 8A:
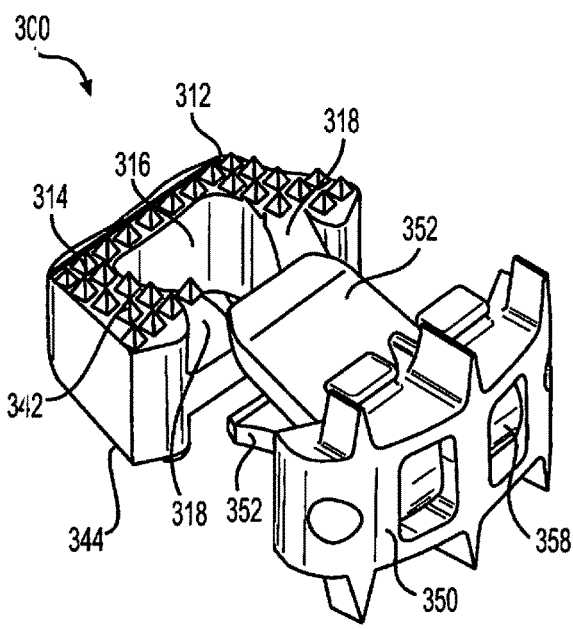
FIGS. 8A and 8B illustrate top perspective views of an alternative embodiment of an interbody fusion device having hinged blades.
Figure 8B:
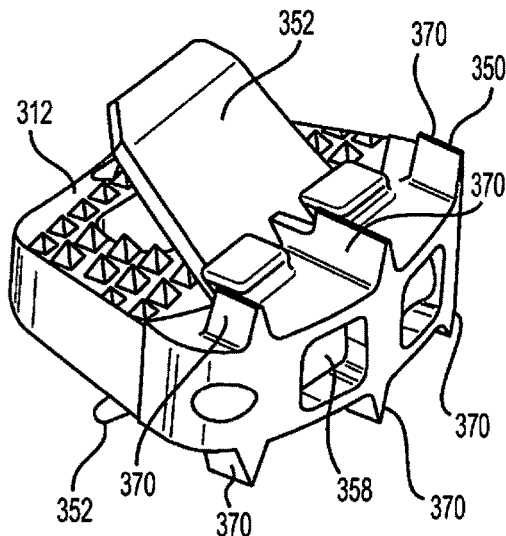

FIGS. 8A and 8B illustrate top perspective views of an alternative embodiment of an interbody fusion device 300 having hinged blades 352. FIG. 8A shows the device 300 disassembled, while FIG. 8B shows the device 300 assembled and configured to be engaged into adjacent vertebrae. The interbody fusion device 300 includes a spacer body 312 and an end member 350 configured to be affixed to the spacer body 312. The spacer body 312 may be in the form of a spacer or cage having an opening 316 that may serve as a graft opening for receiving graft material. The spacer body 312 can include one or more protrusions 314, for example, in the form of teeth, ridges, or ribs on either or both of its superior and inferior surfaces 342, 344 to prevent expulsion of the spacer body 312 between adjacent vertebrae. As shown, the spacer body 312 is configured to have a plurality of teeth on a least a portion of its superior and inferior surfaces 342, 344.

The spacer body 312 includes at least one ramped surface 318. The ramped surface 318 may be positioned on a portion of the superior and/or inferior surfaces 342, 344 on a proximal portion of the spacer body 312 proximate to the end member 350. The ramped surface 318 may include an angled or tapered surface configured to engage a blade 352. The angle of the ramped surface 318 may range from about 1-70°, about 5-60°, about 10-40°, or about 15-30° relative to a horizontal axis. As shown in FIG. 8A, the spacer body 312 may include two ramped surfaces 318 on the superior surface 342 and two identical ramped surfaces 318 on the inferior surface 344 (not shown). The ramped surfaces 318 may be angled such that they extend from a central portion of the spacer body 312 and increase in height outward toward the lateral portions of the spacer body 312.

The spacer body 312 can be removably coupled, attached, or affixed to the end member 350. The spacer body 312 can be attached to the end member 350 by a coupling mechanism, friction fit, interference fit, or any other connection means. For example, the spacer body 312 and the end member 350 may be assembled together using, alone or in combination, a dovetail assembly, dowel pins, hooks, staples, screws, adhesives, and the like, or any suitable fasteners known in the art. The end member 350 may include upper and lower surfaces having one or more torsional stabilizers 370 extending therefrom configured to prevent or minimize torsional motion of the implant 300 once implanted. The torsional stabilizers 370 may act as extensions or fins, which may serve as knife edges to further purchase into the bone of the adjacent vertebrae and/or serve as a stop to abut anterior aspects of the adjacent vertebrae. The torsional stabilizer 370 may include a spiked or pointed projection or extension configured to engage adjacent vertebrae. The torsional stabilizers 370 may be provided at any suitable locations. For example, as shown in FIG. 8B, the torsional stabilizers 370 may be provided proximate to the lateral sides of the end member 350 and are also provided substantially medially on the end member 350 projecting superiorly and inferiorly from both the upper and lower surfaces, respectively.

The end member 350 houses one or more blades 352. The blade 352 may have an elongated, relatively thin structure. The blade 352 may be substantially straight and flat or may be curved. The blade 352 may have any suitable length and width. For example, the blade 352 may have a length substantially the same as the spacer body 312 and a width that is substantially the same as the opening 316 in the spacer body 312. The blade 352 may have a sharpened distal edge to facilitate insertion into the adjacent vertebrae. The distal edge may also be beveled or chamfered at the corners.

The one or more blades 352 may be attached together via a hinge 358. For example, the hinge 358 may be in the form of a cantilevered v-spring with a cross-sectional configuration in the form of a V connecting two blades 352. The hinge 358 may include a living hinge, barrel hinge, piano hinge, ball and socket type hinge, spring, or other suitable hinge known in the art. In one embodiment, the hinge 358 may include a living hinge connecting the blades 352. Living hinges may include one-piece flexing devices or functional hinges having a flexing zone between the blades 352. The living hinge may be constructed of pliant and/or flexible materials having properties which tolerate the repeated tension and compression of the opposing surfaces (i.e., the blades 352). The end member 350 may include one or more openings or windows providing visualization of the blades 352 and/or hinge 358.

As the spacer body 312 is attached or affixed to the end member 350, the one or more hinged blades 352 engage the ramped surfaces 318 of the spacer 312, thereby causing the blades 352 to spread apart and expand outwardly. The blades 352 may have a first, collapsed orientation where the angle between the blades 352 is small and a second, expanded orientation where the angle between the blades 352 is increased to be larger than in the collapsed orientation. The blades 352 are configured to engage one or more adjacent vertebral bone members when in the expanded orientation.

In some embodiments, the body portion 312 is configured to be inserted into a disc space prior to inserting and attaching the end member 350. After clearing a disc space and performing a total or partial discectomy, the body portion 312 can be inserted first into a desirable location. Afterwards, the end member 350 with the one or more blades 352 connected thereto can be attached to the body portion 312. During engagement between the body portion 312 and the end member 350, the blades 352 extend outwardly and into adjacent bone members. In other embodiments, the body portion 312 can be pre-assembled with the end member 350 prior to inserting the interbody fusion device 300 in a disc space.

Figure 9B:
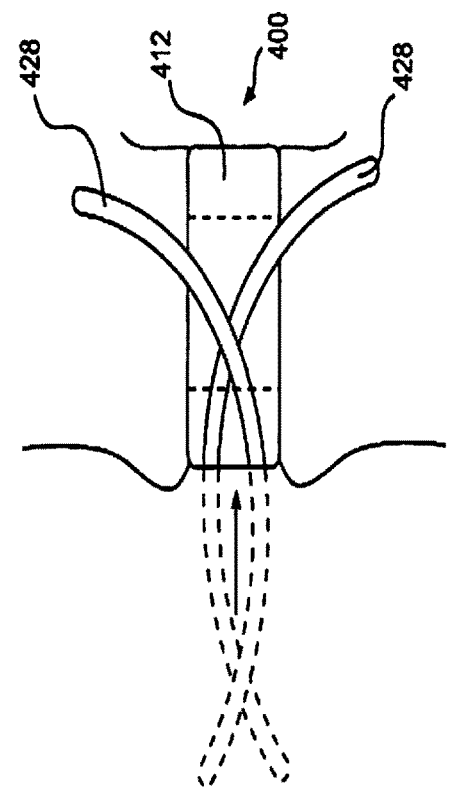
FIGS. 9A and 9B illustrate an alternative interbody fusion device having deployable straight or curved nails.
Figure 10B:
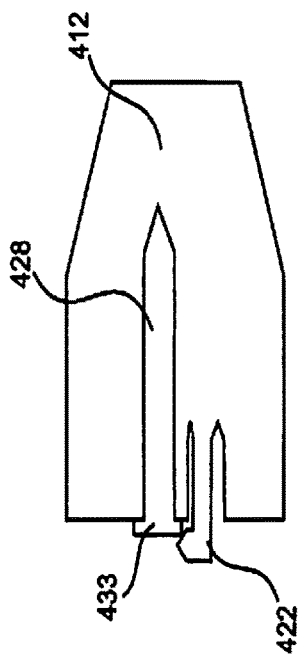
FIGS. 10A and 10B illustrate a spring tab feature on the embodiment depicted in FIGS. 9A and 9B.
Figure 9A:
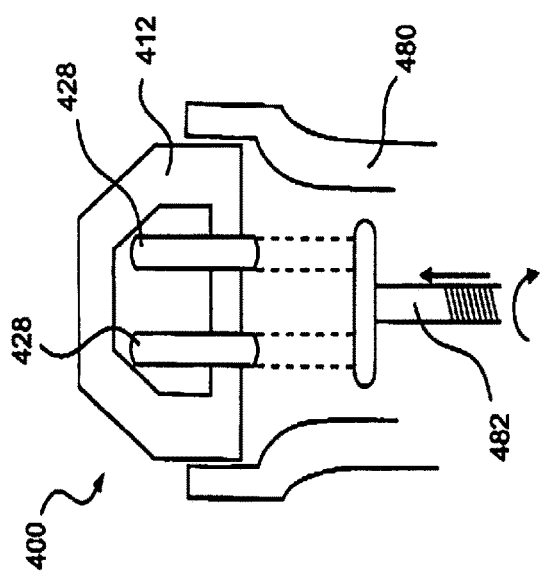
Figure 10A:
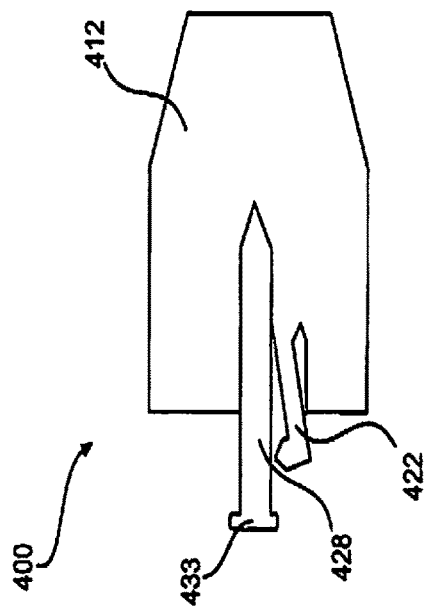

FIGS. 9A and B and FIGS. 10A and B illustrate an alternative interbody fusion device 400 having deployable straight or curved fixation members 428, such as nails. The interbody fusion device 400 may include any of the fusion devices described herein. FIG. 9A depicts a top view of a spacer body 412 and an insertion instrument 480 configured for inserting two fixation members 428 through the spacer body 412. The insertion instrument 480 may include a pusher element 482, which may be threaded, for example. As the pusher element 482 is advanced and/or rotated in the direction of the arrows, the fixation members 428 are advanced into the spacer body 412 and deployed into the adjacent vertebrae. The pusher element 482 may be ratchet or lever operated, for example. The instrument 480 may be able to deploy multiple fixation elements 428 simultaneously.

FIG. 9B depicts a side view of the embodiment shown in FIG. 9A where the fixation members 428 (initially depicted as dashed lines) enter the spacer body 412 to be deployed within the superior and inferior vertebral bodies. For example, the devices 400 may have a minimum of one in the superior direction and one in the inferior direction which are pressed through the spacer body 412 and retained partially within the spacer body 412. The fixation members 428 may be straight or curved and may include any of the fixation members described herein.

The fixation member 428 may be held within the spacer body 412 with an additional component, such as a blocking mechanism. The blocking mechanism may include any of the blocking mechanisms described herein, such as a blocking screw. Alternatively, the fixation member 428 could be held in position with a spring tab 422. FIG. 10A illustrates a top view of the spacer body 412 having the spring tab 422 in an initial position before the fixation member 428 is fully inserted, and FIG. 10B illustrates a top view of the same spacer body 412 in a final position with the fixation member 428 fully inserted and the spring tab 422 engaged to retain the fixation member 428. The spring tab 422 may include a flexible portion that flexes as the fixation member 428 is inserted into the device 400, and blocks the fixation member 428 once it is fully inserted. As shown in FIG. 10B, after insertion, the fixation member 428 is blocked by the spring tab 422 and is unable to back out of position. In addition, the fixation members 428 (e.g., nails) may be prevented from being pushed too far into the vertebral body by a head 433, for example, on each nail, or by limits fixed to the deploying inserter instrument 480.

Figure 11A:
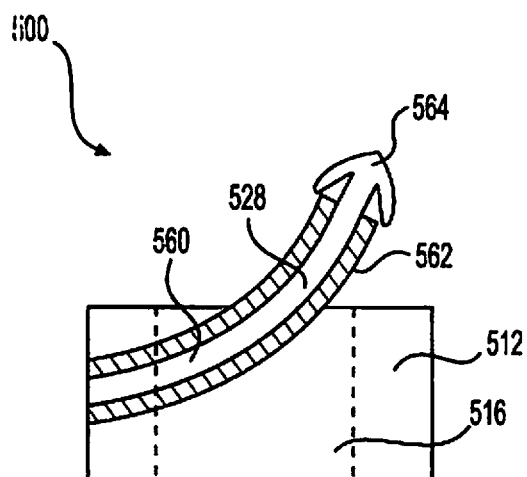
FIGS. 11A-D provide an alternative interbody fusion device having deployable two-piece nails.
Figure 11B:
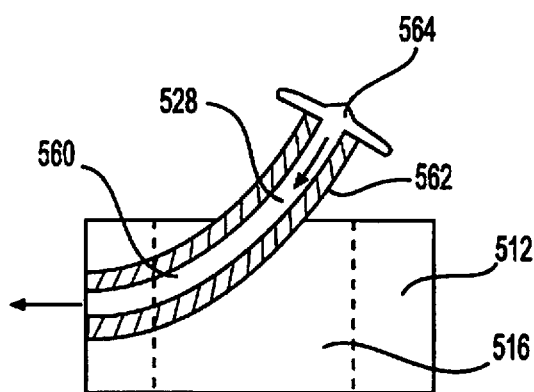

FIGS. 11A-D illustrate an alternative interbody fusion device 500 having deployable two-piece fixation members 528, such as nails, that could be curved or straight. The interbody fusion device 500 may include any of the fusion devices described herein. FIG. 11A depicts a side view of a spacer body 512 including two-piece fixation member 528 extending therethrough and into an adjacent vertebra in an initial, insertion configuration. FIG. 11B depicts a side view of the spacer body 512 with the fixation member 528 in a final, deployed configuration.

Figure 11C:
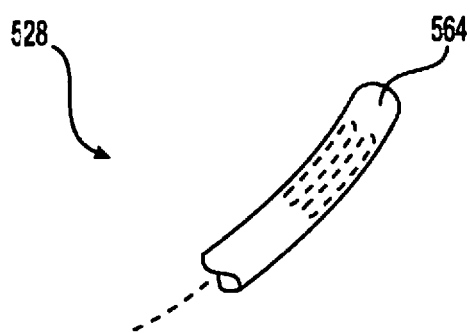
Figure 11D:
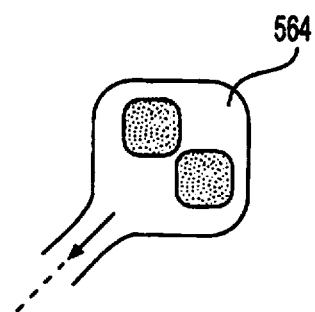

In some embodiments, the two-piece fixation member 528 can comprise an inner portion 560 and an outer sleeve 562. The assembled inner and outer parts 560, 562 can be pushed into a vertebral bone together, for example, as shown in FIG. 11A. Once the assembly is inserted into a desired location into bone, the inner portion 560 is capable of being pulled back slightly toward the outer sleeve 562 and away from the insertion direction, as the arrow depicts in FIG. 11B. This action deforms and splays the tip 564 of the fixation member 528, thereby advantageously helping to secure the fixation member 528 and/or the inner portion 560 in the bone. The deployed configuration may help to prevent back out of the fixation member 528. In addition, this method may compressively load the graft within the graft window 516 in the spacer body 512. Similarly, FIG. 11C shows an alternative tip 564 for the fixation member 528 in the initial, insertion configuration, and FIG. 11D shows the tip 564 in the final, deployed configuration. As above, the assembled inner portion 560 and outer sleeve 562 can be inserted into a vertebral bone together, and once the assembly is pushed into a desired location in the bone, the inner portion 560 is pulled opposite to the insertion direction to expand or inflate the tip 564 of the fixation member 528.

Figure 12A:
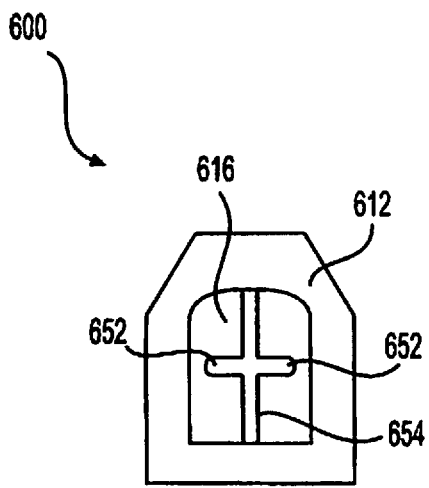
FIGS. 12A-F show an alternative interbody fusion device having one or more sets of fins that cut through adjacent bone.
Figure 12B:
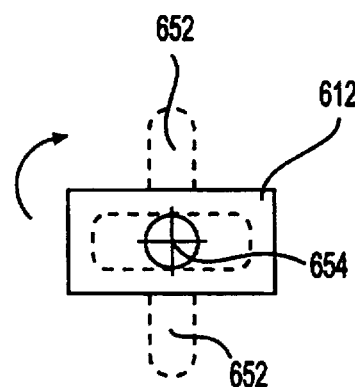
Figure 12C:
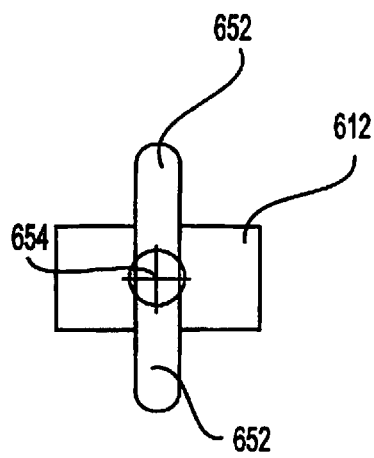
Figure 12D:
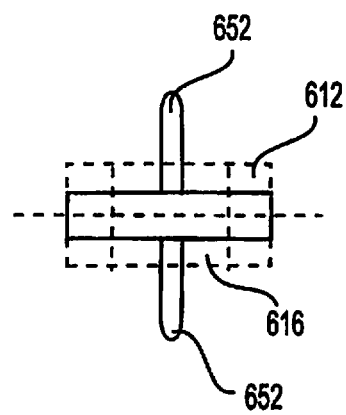
Figure 12E:
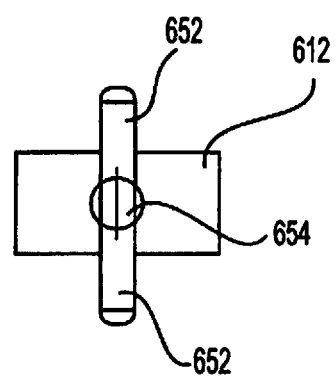
Figure 12F:
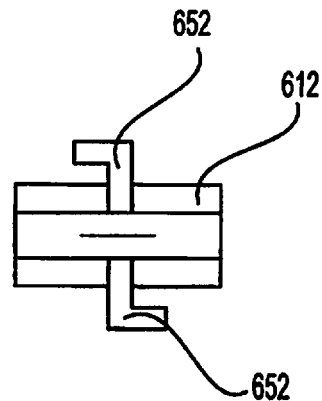

Similar to the embodiments depicted in FIGS. 6 and 7, FIGS. 12A-F show alternative interbody fusion devices 600 having one or more sets of fins 652 that cut through adjacent bone. FIG. 12A shows the device 600 having a spacer body 612. The spacer body 612 may be in the form of a spacer or cage having opening 616 that may serve as a graft opening for receiving graft material. As shown, the fusion device 600 may have at least one central shaft 654 with one or more sets of fins 652. The fins 652 may be initially contained within the opening 616 as shown in FIG. 12A. The fins 652 may be activated by a driver, for example, and the fins 652 may retain and secure the device 600 once deployed, as shown in FIG. 12B. The one or more sets of fins 652 can be straight or have hooked shapes. FIGS. 12C and D depict a similar set of fins 652 in a deployed state where the fins 652 are larger than the graft opening 616. FIGS. 12E and F depict a similar set of fins 652 in a deployed state where the fins 652 have a bent or hooked configuration (e.g., L-shaped, J-shaped, C-shaped, or the like). The fins 652 may be all of the same type, height, and configuration or may be different on a given device 600.

Rotation of the central shaft 654 causes deployment of the fins 652 such that the fins 652 can engage an upper and/or lower vertebrae. Rotation of the shaft 654 in a first direction will cause deployment of the fins 652, for example in a substantially vertical orientation, whereas rotation of the shaft 654 in a second opposite direction will cause retraction of the fins 652, for example, in a substantially horizontal orientation. In particular, the fins 652 may be rotated about 90° between the retracted and deployed positions.

Figure 13A:
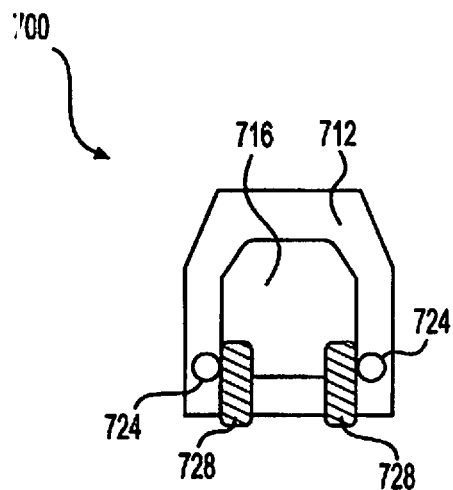
FIGS. 13A and 13B show an alternative interbody fusion device having deployable spikes through a rack and pinion design.
Figure 13B:
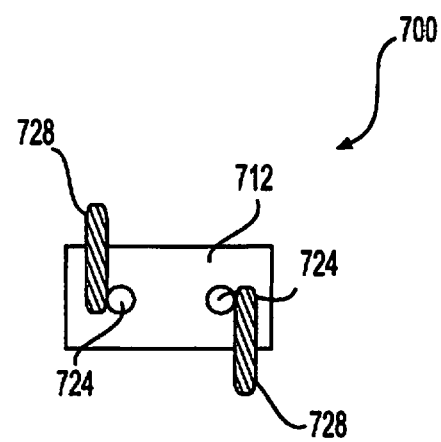

FIGS. 13A and B show an alternative interbody fusion device 700 having deployable fixation members 728 through a rack and pinion design. Similar to the other devices described herein, FIG. 13A depicts a top view of a spacer body 712 with a graft opening 716. FIG. 13B depicts a side view of the device 700. One or more fixation members 728 may be connected or coupled to the spacer body 712 with a rack and pinion 724. The rack and pinion 724 may include circular gear or pinion, which engages teeth on a linear gear or rack. The rack and pinion 724 may convert rotational motion, for example, from a driver, into linear motion of the fixation members 728. The fixation members 728 may include screws, nails, shims, spikes, staples, pins, or the like. In an exemplary embodiment, the fixation members 728 are in the form of deployable spikes or nails. Alternatively, the interbody fusion device 700 can have deployable screws via a worm gear mechanism (see FIG. 21).

Figure 14:
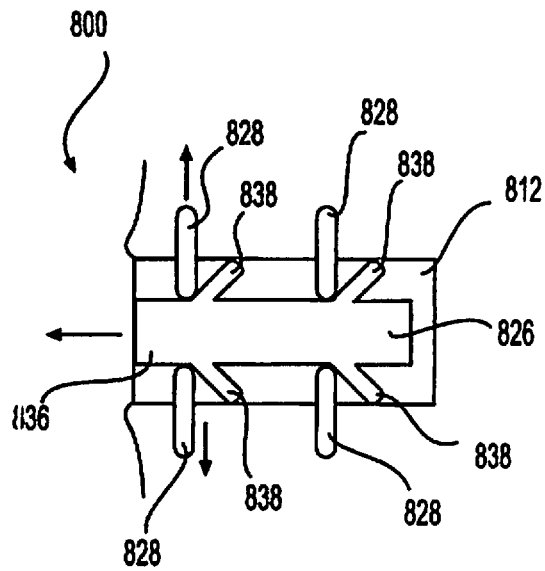
FIG. 14 illustrates an alternative interbody fusion device having deployable spikes using movable ramps.

FIG. 14 illustrates an alternative interbody fusion device 800 using one or more movable ramps 826. The ramp 826 may have a translation member 836 having one or more ramped surfaces 838 that engage deployable fixation members 828, such as a spikes. As shown in FIG. 14, the translation member 836 of the device 800 can include at least two upper ramps 838 connected via a bridge, and two lower ramps 838 connected via a bridge. Each of the ramped surfaces 838 is configured to engage a deployable fixation member 828. As the translation member 836 is translated (e.g., via a rotatable actuation member) in a first direction, the ramped surfaces 838 engage the fixation members 828, thereby deploying them through openings in the upper and lower surfaces of the fusion device 800. Thus, the ramped surfaces 838, when translated linearly, cause the fixation members 828 to expand outwardly and engage the adjacent vertebrae. Although two ramped surfaces 838 are depicted to engage two fixation members 828 on each of the upper and lower surfaces, any suitable number of ramped surfaces 838 and fixation members 828 may be used.

Figure 15A:
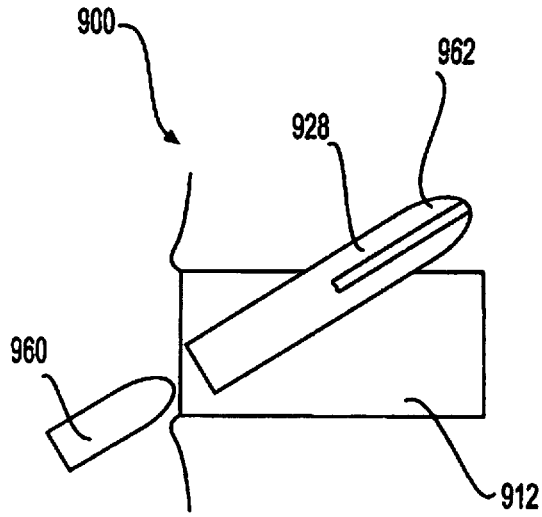
FIGS. 15A and 15B show an alternative interbody fusion device having a deformable spike or nail.
Figure 15B:
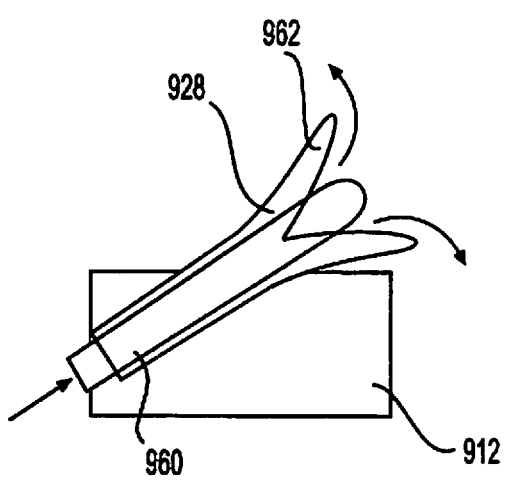

FIGS. 15A and B show an alternative interbody fusion device 900 having deformable fixation members 928, such as a nails or a spikes. The interbody fusion device 900 may include any of the fusion devices described herein. FIG. 15A depicts a side view of a spacer body 912 including a first member 962 extending therethrough and into an adjacent vertebrae in an initial, insertion configuration. FIG. 15B depicts a side view of the spacer body 912 with the fixation member 928 in a final, deployed configuration. The deformable fixation member 928 may be comprised of a two-piece design whereby a first member or outer sleeve 962 is first introduced into the vertebral body. A second member or inner portion 960 is then threaded or otherwise pushed through the first member 962. The tip of the first member 962 is configured to splay and deform as shown in FIG. 15B. The deployed configuration may help to prevent back out of the fixation member 928. The fixation members 928 may be curved or straight before and/or after being deployed.

Figure 16A:
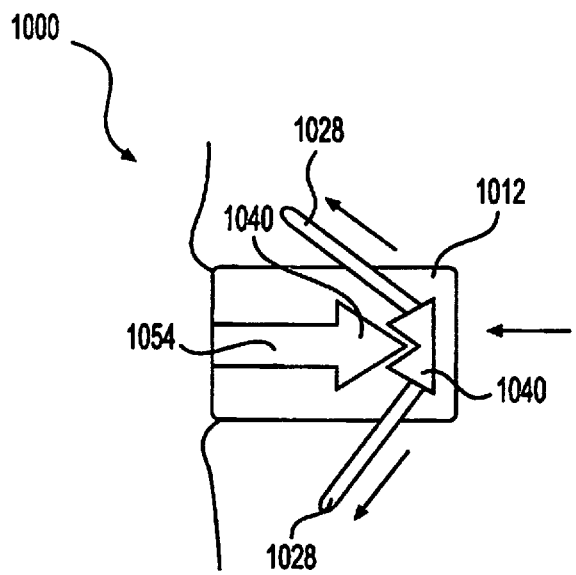
FIGS. 16A-C show an alternative embodiment of an interbody fusion device having deployable spikes or nails.
Figure 16B:
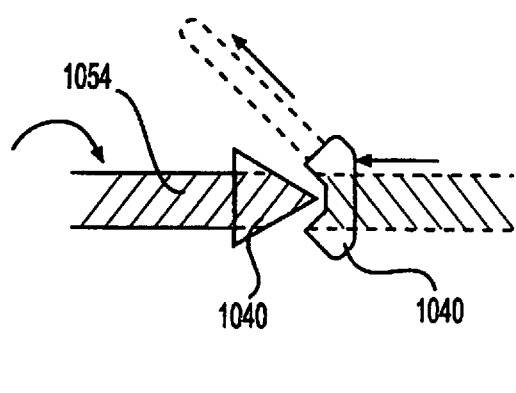
Figure 16C:
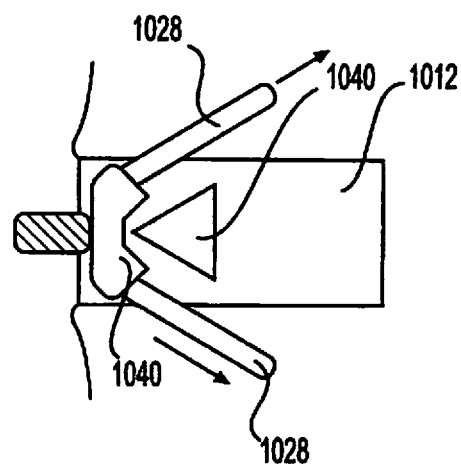

FIGS. 16A-C show an alternative embodiment of an interbody fusion device 1000 having deployable fixation members 1028, such as spikes or nails. The interbody fusion device 1000 may include any of the fusion devices described herein. FIG. 16A depicts a side view of a spacer body 1012 including fixation members 1028 extending therethrough and into adjacent vertebrae in a deployed configuration. The device 1000 may use a threaded shaft 1054 and two or more keyed parts 1040 that are internally threaded and move in different directions when the threaded shaft 1054 is turned. This motion allows the fixation members 1028, which may be attached to the keyed parts 1040, to deploy in an anterior-superior and anterior-inferior direction as shown (FIG. 16A), as well as in the posterior-superior and posterior-inferior directions (FIG. 16C), if preferred.

Figure 17A:
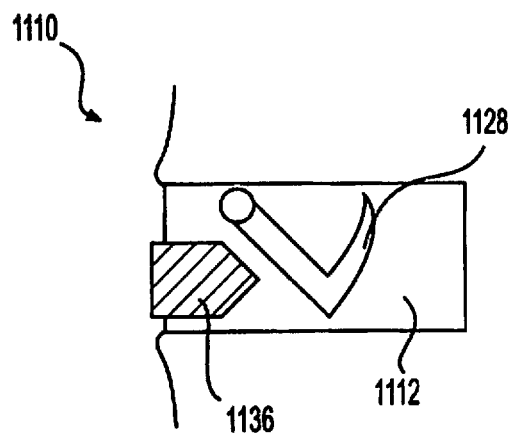
FIGS. 17A and 17B depict an alternative interbody spinal fusion device that includes an internal pivoting hook member.
Figure 17B:
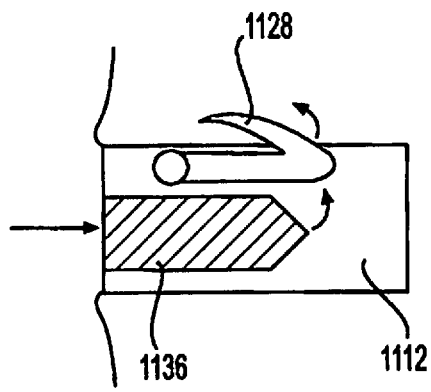

FIGS. 17A and B show an alternative interbody spinal fusion device 1100 that includes an internal pivoting hook member 1128 which is made to pivot by an actuation member 1136. The interbody fusion device 1100 may include any of the fusion devices described herein. FIG. 17A depicts a side view of a spacer body 1112 including hook member 1128 retracted within the spacer body 1112. FIG. 17B shows a side view of the spacer body 1112 with the hook member 1128 extending therefrom and into an adjacent vertebra in a deployed configuration. The translation or actuation member 1136 is configured to translate and push the pivoting hook 1028 outward such that it is configured to grip an intervertebral member. The actuation member 1136 may include a ramped surface or beveled tip to provide for uniform movement of the hook member 1128. The actuation member 1136 may be threaded or pushed, and may be locked into position to deploy the hook member 1128.

Figure 18A:
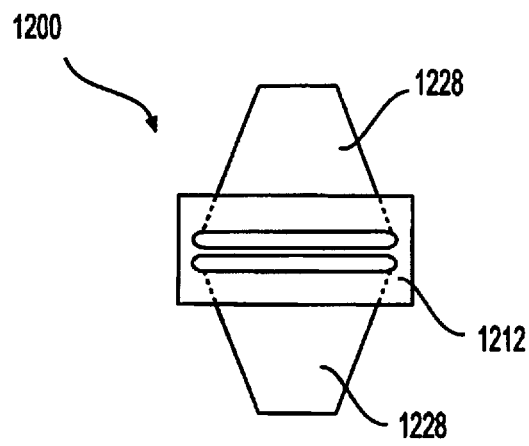
FIGS. 18A-E show an alternative interbody spinal fusion device that includes deployable tangs.
Figure 18B:
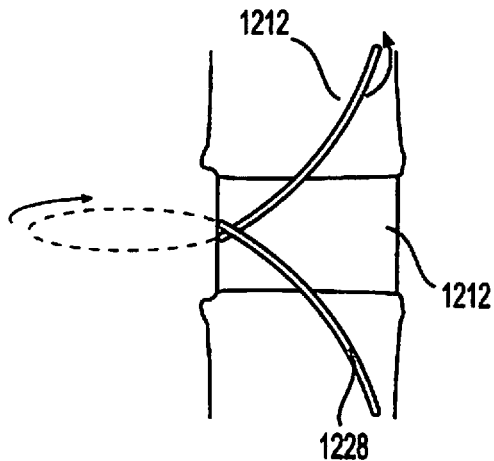
Figure 18C:
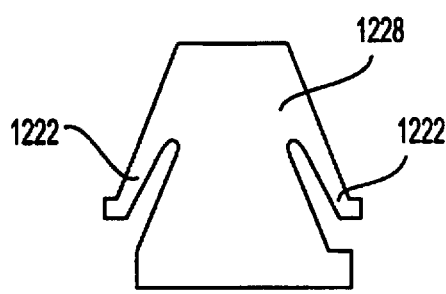
Figure 18D:
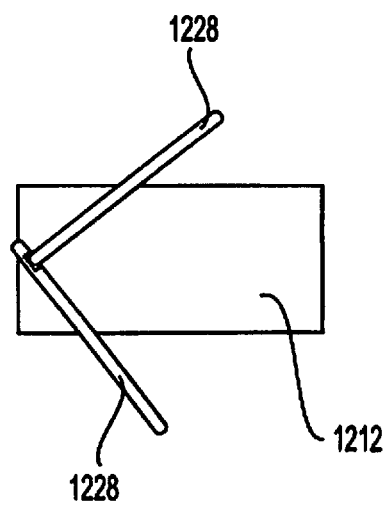
Figure 18E:
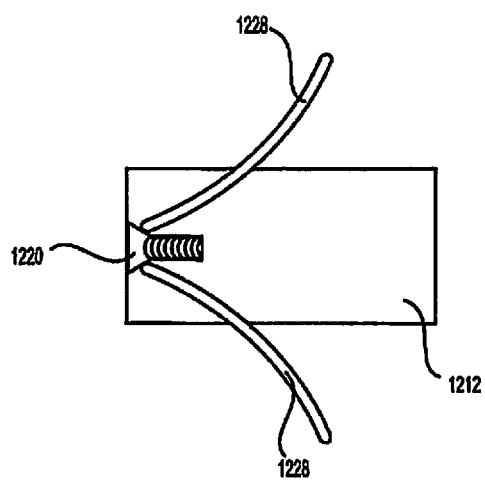

FIGS. 18A-E show an alternative interbody spinal fusion device 1200 that includes deployable fixation members 1228, such as tangs. FIG. 18A depicts a front view of a spacer body 1212 with fixation members 1228 configured to extend superiorly and inferiorly. The fixation members 1228 may be pressed through the spacer body 1212 (e.g., made of PEEK) and embedded into adjacent vertebral bodies. The fixation members 1228 may be tapered such that a distal end of the fixation member 1228 is narrower than a proximal portion of the fixation member 1228 residing within the spacer body 1212. The distal end of the fixation member 1228 may have a sharpened edge to facilitate insertion into the adjacent vertebrae. FIG. 18B depicts a side view of the spacer body 1212 with the fixation members 1228 extended therethrough. As shown in FIG. 18C, the fixation members 1228, for example, in the form of tangs, can be prevented from moving out of the spacer body 1212 by one or more spring retainers 1222 on the fixation members 1228 and/or on the spacer body 1212. The spring retainers 1222 may include a flexible portion that flexes as the fixation member 1228 is inserted into the device 1200. As shown in FIG. 18E, the fixation member 1228 could also be locked in position through a third component, such as a blocking mechanisms 1220 (e.g., a blocking screw). The fixation members 1228 may also be locked in position by locking the proximal ends together as shown in FIG. 18D. The fixation members 1228 may include tangs that are flat or curved. The fixation members 1228 may be made from metal including hydroxyapatite (HA) coated metal.

To assist in providing easy insertion of the fusion devices above, various instruments are provided. In particular, the instruments help facilitate inline operation. In many locations of the spine, such as the most caudal or most cephalad cervical disc spaces (e.g., C5-C6/C6-C7 and C2-C3), it can be hard to insert the fusion devices due to interferences with the chin or chest. The same is true for caudal lumbar levels (e.g., L5-S1), where insertion can be complicated due to interference with tissue. The following descriptions include alternative interbody fusion devices, some of which facilitate inline operation.

FIG. 19 illustrates an interbody fusion device 1300 having one mechanism for facilitating inline operation. The fusion device 1300 comprises a spacer body 1312 with an end member 1350. The device 1300 includes a combination of two angled holes 1366 in the spacer body 1312 and corresponding straight holes 1368 in the end member 1350. A fixation member, such as a bone screw having a polyaxial head and a shaft attached thereto, is insertable through the end member 1350 and the spacer body 1312. During insertion, the bone screw would be inserted straight with an appropriate sleeved instrument. As the bone screw is inserted, the sleeve will move back and expose the polyaxial head of the bone screw. As the bone screw is inserted further, the shaft of the screw hits one of the predrilled angled holes 1366 in the spacer body 1312 while the polyaxial head engages the straight hole 1368 in the end member 1350. In other words, the addition of a polyaxial head on the bone screw allows the shaft to angle through the angled holes 1366. In some embodiments, the shaft is threaded and can engage an adjacent vertebral body. Using this design, the interbody fusion device 1300 can be inserted via an inline operation until the shaft of the bone screw angles down the angled hole 1366.

FIGS. 20A and 20B illustrate a universal joint (e.g., a ball joint) that can be built in the head 1431 of a bone screw 1430 to provide polyaxial adjustability. In some embodiments, the universal joint can be used with the embodiment in FIG. 19 to provide a polyaxially adjustable bone screw 1430. The screw head 1431 can comprise a spherical trough 1429 with a slot perpendicular to the longitudinal axis of the screw 1430 which mates with a screw driver 1480, for example, having projections configured to mate with the trough 1429. This design allows for driving of the bone screw 1430 into a fusion device at any angle, thereby allowing the shaft of the driver 1480 to remain parallel to a disc space if desired.

FIG. 21 illustrates how deployable fixation members, such as nails, fins etc. can be actuated by a worm drive. In particular, the worm drive may include a worm 1546 and/or worm wheel 1548 with teeth at an angle. The worm 1546 may be in the form of a screw, which meshes with the worm wheel 1548. The worm wheel 1548 may have a wheel-like body with a plurality of teeth positioned along the periphery of the body and which radially extend outward. The worm wheel 1548 may have teeth machined at an angle configured to interlock with the worm 1546.

FIG. 22 illustrates fixation members, such as spikes 1528, having one or more deployable barb wires 1572. The barb wires 1572 may be deployed through the spike 1528. For example, the spike 1528 may be hammered in through the spacer body 1512, and the barbs 1572 may be deployed simultaneously or after the spike 1528 has been fully implanted. The barbs 1572 may extend through a distal portion of the spike 1528. The ends of the barbs 1572 may have a sharp point, and the barbs 1572 may be curved to enhance fixation. The spikes 1528 may be curved or straight, and may include any of the fixation members described herein.

FIG. 23 illustrates an alternative interbody fusion device including a straight or curved rack and pinion mechanism with an inline actuated pinion 1576 driving a curved or straight rack 1574 into a vertebral body. The rack 1574 has a longitudinal body and includes a plurality of teeth on at least one side of the rack 1574. The pinion 1576 has a wheel-like body with a plurality of teeth positioned along the periphery of the body and which radially extend outward. The pinion 1576 translates rotation motion (e.g., from a driver) to linear or curvilinear movement of the rack 1574, thereby causing the rack 1574 to be deployed into the adjacent vertebral space. In this case, the rack 1574 may be acting and functioning as the fixation member.

FIG. 24 illustrates a keeled connection between a spacer and a vertebral body. The keeled connection may include a plurality of keels 1578, for example, which are deployable from the superior and/or inferior surfaces of the device. The keels 1578 may be in the form of teeth, ridges, ribs, extensions, fins, or the like. The keels 1578 may include a sharp edge to further purchase into the bone of the adjacent vertebrae. The keels 1578 can be deployed similar to any of the fixation members including nails, shims, or fins as discussed above.

There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for implanting an implant between a superior vertebral body and an inferior vertebral body, said method comprising:
   providing a spacer having an upper surface and a lower surface, wherein the upper surface is configured to engage the superior vertebral body and the lower surface is configured to engage the inferior vertebral body, the spacer having first and second angled fixation holes;
   attaching an end member to the spacer, the end member having first and second straight fixation holes meeting the respective first and second angle fixation holes at a predetermined angle;
   inserting the spacer and the end member between the superior vertebral body and the inferior vertebral body;
   extending a first polyaxial fixation member through the first straight fixation hole of the end member and then through the first angled fixation hole so as to allow a shaft of the first polyaxial fixation member to be inserted straight into the first straight fixation hole and then angle through the first angled fixation hole, a polyaxial head of the first polyaxial fixation member allowing its shaft to angle through the first angled fixation hole;
   extending a second fixation member through the second straight fixation hole of the end member and then through the second angled fixation hole so as to allow a shaft of the second polyaxial fixation member to be inserted straight into the second straight fixation hole and then angle through the second angled fixation hole, a polyaxial head of the second polyaxial fixation member allowing its shaft to angle through the second angled fixation hole; and
   blocking the first fixation member and the second fixation member to prevent backout.

2. The method of claim 1, wherein the spacer comprises an opening extending from the upper surface to the lower surface.

3. The method of claim 1, wherein the spacer is formed of PEEK.

4. The method of claim 1, wherein the spacer comprises a female recess and the end member comprises a male projection insertable into the female recess to attach the spacer to the end member.

5. The method of claim 1, wherein a dovetail assembly is formed between the spacer and the end member.

6. The method of claim 1, wherein the first fixation member shaft comprises a straight shim.

7. The method of claim 1, wherein the first fixation member shaft comprises a curved shim.

8. The method of claim 1, wherein the polyaxial head of the first fixation member includes an opening for receiving an insertion instrument.

9. The method of claim 1, wherein the first fixation member continuously tapers from the polyaxial head to a distal end of the first fixation member.

10. The method of claim 1, wherein the first fixation member includes splines.

11. A method for implanting an implant between a superior vertebral body and an inferior vertebral body, said method comprising:
    providing a spacer comprising an upper surface and a lower surface, wherein the upper surface includes one or more protrusions and the lower surface comprises one or more protrusions, the spacer having a first angled fixation opening;
    attaching an end member to the spacer, wherein the end member includes a first straight opening, a second opening and a third opening, the first straight opening meeting the first angle fixation opening at a predetermined angle;
    inserting the spacer and the attached end member between the superior vertebral body and the inferior vertebral body;
    extending a first fixation member through the first straight fixation opening and then through the first angled fixation opening so as to allow a shaft of the first fixation member to be inserted straight into the first straight opening and then angle through the first angled fixation opening, the first fixation member having a head portion and a distal end;

extending a second fixation member through the second opening;

extending a third fixation member through the third opening, and blocking the first fixation member, the second fixation member, and the third fixation member to prevent backout, wherein the shaft of the first fixation member includes at least one spline extending from the head portion to the distal end.

12. The method of claim 11, wherein the first fixation member is straight.

13. The method of claim 12, wherein the end member is formed of a metallic material.

14. The method of claim 11, wherein the first fixation member is curved, while the second fixation member and the third fixation member are straight.

15. The method of claim 11, wherein the first fixation member extends in an upward angle relative to the spacer and the second fixation member and the third fixation member each extend in a downward angle relative to the spacer.

16. The method of claim 11, wherein the spacer is attached to the end member via a dovetail connection.

17. The method of claim 11, wherein a first blocking mechanism is turned for blocking the first fixation member and the second fixation member from backing out.

18. The method of claim 17, wherein a second blocking mechanism is turned for blocking the first fixation member and the third fixation member from backing out.

19. The method of claim 11, wherein the spacer is formed of PEEK.

20. The method of claim 11, wherein the spacer further comprises an opening extending from the upper surface to the lower surface.

* * * * *